US010266842B2

(12) United States Patent
Vilcinskas et al.

(10) Patent No.: US 10,266,842 B2
(45) Date of Patent: Apr. 23, 2019

(54) POLYPEPTIDES AGAINST PLANT PATHOGENIC FUNGI

(71) Applicant: Fraunhofer-Gesellschaft zur Foerderung der angewandten Forschung e.V., Munich (DE)

(72) Inventors: Andreas Vilcinskas, Fernwald (DE); Anne-Kathrin Poeppel, Giessen (DE); Jochen Wiesner, Giessen (DE)

(73) Assignee: Fraunhofer-Gesellschaft Zur Foerderung Der Angewandten Forschung E.V., Munich (DE)

( * ) Notice: Subject to any disclaimer, the term of this patent is extended or adjusted under 35 U.S.C. 154(b) by 399 days.

(21) Appl. No.: 14/766,776

(22) PCT Filed: Jan. 23, 2014

(86) PCT No.: PCT/EP2014/051345
§ 371 (c)(1),
(2) Date: Aug. 10, 2015

(87) PCT Pub. No.: WO2014/124786
PCT Pub. Date: Aug. 21, 2014

(65) Prior Publication Data
US 2016/0002663 A1 Jan. 7, 2016

Related U.S. Application Data

(60) Provisional application No. 61/763,585, filed on Feb. 12, 2013.

(30) Foreign Application Priority Data

Feb. 12, 2013 (EP) ..................................... 13154940

(51) Int. Cl.
| | |
|---|---|
| *A01N 63/02* | (2006.01) |
| *A01N 37/46* | (2006.01) |
| *C07K 14/435* | (2006.01) |
| *C12N 15/82* | (2006.01) |
| *C07K 14/00* | (2006.01) |

(52) U.S. Cl.
CPC ......... *C12N 15/8282* (2013.01); *A01N 37/46* (2013.01); *A01N 63/02* (2013.01); *C07K 14/00* (2013.01); *C07K 14/43577* (2013.01)

(58) Field of Classification Search
None
See application file for complete search history.

(56) References Cited

U.S. PATENT DOCUMENTS

2010/0215765 A1 8/2010 Bexfield et al.

FOREIGN PATENT DOCUMENTS

EP 0798381 10/1997

OTHER PUBLICATIONS

Banzet et al (Plant Science, 2002, 162: 995-1006).*
Database Embl [Online], Mar. 1, 2001, Lc30004A16.g Lucilla cuprina third instar larval cDNA library Lucilla cupring cDNA clone Lc30004A16.g, mRNA sequence. XP002700005.
Aerts et al. The mode of antifungal action of plant, insect, and human defensins, Cell. Mol. Life Sci. 65 (2008) 2069-2079.
Banzet et al. Expression of insect cystein-rich antifungal peptides in transgenic tobacco enhances resistance to a fungal disease. Plant Science 162 (2002) 995-1006.
Bayerisches Landesamt fuer Wasserwirtschaft. Jul. 25, 2005.
Boman. Antibacterial peptides: basic facts and emerging concepts. Journal of Internal Medicine 2003; 254: 197-215.
Coca et al. Enhanced resistance to the rice blast fungus *Magneporthe grisea* conferred by expression of a cecropin A gene in transgenic rice. Planta (2006) 223; 392-406.
Kragol et al. The Antibacterial Peptide Pyrrhocoricin Inhibits the ATPase Actions of DnaK and Prevents Chaperone-Assisted Protein Folding. Biochemistry 2001, 40, 3016-3026.
Langen et al. Transgenic expression of gallerimycin, a novel antifungal insect defensin from the greater wax moth *Galleria melionella*, confers resistance to pathogenic fungi in tobacco. Biol. Chem., vol. 387. pp. 549-557, May 2006.
Levashina et al. Metchnikowin, a novel immune-inducible proline-rich peptide from Drosophiliz with antibacterial and antifungal properties. Eur. J. Biochem. 233. 694-700 (1995).
Marr et al. Antibacterial peptides for therapeutic use: obstacles and realistic outlook. ScienceDirect, Current Opinion in Pharmacology 2006, 6; 468-472.
Hickey. Methods for Enhancing Pesticides for Control of Plant Pathogens. 1986. pp. 116-281.
Weissbach et al. Methods for Plant Molecular Biology. 1988.
Glick et al. Methods in Plant Molecular Biology and BioTechnology. Chapter 6, pp. 67-88.
Osusky et al. Transgenic plants expressing cationic peptide chimeras exhibit broa-spectrum resistance to phytopathogens. Nature Biotechnology, vol. 18, Nov. 2000.
Rahnamaeian et al. Insect peptide metchnikowin confers on barley a selective capacity for resistance to fungal ascomycetes pathogens. Journal of Experimental Botany, vol. 60, No. 14, 410604114, 2009.

(Continued)

*Primary Examiner* — Stephen Uyeno
(74) *Attorney, Agent, or Firm* — Jacobson Holman PLLC

(57) ABSTRACT

The present invention discloses polypeptides comprising an amino acid sequence being identical with at least 12 contiguous amino acid residues of SEQ ID No 2. The polypeptides according to the invention are effective against fungi, especially against fungi causing plant diseases, and against fungi colonizing agricultural products. The invention further discloses processes for preparing such polypeptides, and nucleic acids coding for such polypeptides. In addition, the invention relates to processes and preparations for treating plants using the polypeptides according to the invention, and to the use of the nucleic acids according to the invention for producing crops that are protected against damage from fungi.

13 Claims, 11 Drawing Sheets
Specification includes a Sequence Listing.

(56) References Cited

OTHER PUBLICATIONS

Bundesinstitut fuer gesundheitlichen Verbraucherschutz und Veterinarmedizin, Jun. 7, 2001.
Schisler et al. Biological control of fusarium head blight of wheat and deoxynivalenol levels in grain via use of microbial antaginists. Mycotoxins and Food Saferty, 2002, pp. 53-69.
Vaara. New approaches in peptide antibiotics. ScienceDirect, Current Opinion in Pharmacology, 2008, 9; 571-576.
Van der Weerden et al. The plant defensin, NaD1, enteres the cytoplasm of Fusarium Oxysporum Hyphae, Journal o Biological Chemistry, vol. 283, No. 21, May 23, 2008.
Yevfushenko et al. Pathogen-induced expression of a cecropin A-melittin antimicrobial peptide gene confers antifungal resistance in transgenic tobacco. Journal of Experimental Botany, vol. 56, No. 416, pp. 1685-1695, Jun. 2005.
Zasloff. Antimicrobial peptides of multicellular organisms. Nature. vol. 415, Jan. 24, 2002.
Lee et al., Accession No. JG407441, Lc30004A16.g Lucilia cuprina third instar larval cDNA library Lucilia cuprina cDNA clo Lc30004A16.g, mRNA sequence, GenBank [online], May 19, 2011, http://www.ncbi.nlm.gov.nucest/JG407441.

\* cited by examiner

SEQUENCE LISTING

```
<160> NUMBER OF SEQ ID NOS: 8

<210> SEQ ID NO 1
<211> LENGTH: 77
<212> TYPE: PRT
<213> ORGANISM: Lucilia sericata

<400> SEQUENCE: 1

Gln His Gly Tyr Gly Ala Gly Gly His Gly Gln Gln Gly Tyr Gly Ser
1               5                   10                  15

Gln His Ser Ser His Ala Pro Gln Gly Gly His Val Val Arg Glu Gln
            20                  25                  30
```

Gly Phe Ser Gly His Val His Glu Gln Gln Ala Gly His His Glu
            35                  40                  45

Ala Gly His His Glu Gln Ala Gly His His Glu Gln Ser Gly Gln Gln
 50                  55                  60

Val His Gly Gln Gly His Gly Tyr Lys Ser His Gly Tyr
 65                  70                  75

<210> SEQ ID NO 2
<211> LENGTH: 73
<212> TYPE: PRT
<213> ORGANISM: Lucilia sericata

<400> SEQUENCE: 2

Gln His Gly Tyr Gly Ala Gly Gly His Gly Gln Gln Gly Tyr Gly Ser
 1               5                   10                  15

Gln His Ser Ser His Ala Pro Gln Gly Gly His Val Val Arg Glu Gln
            20                  25                  30

Gly Phe Ser Gly His Val His Glu Gln Gln Ala Gly His His His Glu
            35                  40                  45

Ala Gly His His Glu Gln Ala Gly His His Glu Gln Ser Gly Gln Gln
 50                  55                  60

Val His Gly Gln Gly His Gly Tyr Lys
 65                  70

<210> SEQ ID NO 3
<211> LENGTH: 231
<212> TYPE: DNA
<213> ORGANISM: Lucilia sericata

<400> SEQUENCE: 3
caacacggct atggtgccgg tggccatggc caacaaggct atggtagcca acatagcagt      60
catgctcccc aaggtggaca tgttgtccgt gaacaaggtt ttagtggtca tgttcatgaa     120
caacaggctg gcatcatca tgaagctggc catcatgagc aagctggtca tcatgaacaa     180
tctggtcaac aagttcatgg tcaaggtcat ggctataaaa gtcatggtta t             231

<210> SEQ ID NO 4
<211> LENGTH: 269
<212> TYPE: DNA
<213> ORGANISM: Lucilia sericata

<400> SEQUENCE: 4
atggtaggtc tcaaatgcag catggctatg gagcgggtgg acatggccag cagggttacg      60
gctctcagca cagcagtcat gctccgcaag gtggccatgt cgttcgcgaa cagggctttt    120
ccggtcacgt acacgagcag caagcaggcc atcaccatga gccggccat cacgaacaag     180 cgggtcacca tgaggagtca gggcagcaag tgcatgggca aggtcatggc tacaaatcgc    240
acgggtatta aagcgctgag acctaccat                                       269

<210> SEQ ID NO 5
<211> LENGTH: 43
<212> TYPE: DNA
<213> ORGANISM: Primer

<400> SEQUENCE: 5
tgaggtaccg acgacgacga caagcagcat ggctatggag cgg                       43

<210> SEQ ID NO 6

-continued

```
<211> LENGTH: 53
<212> TYPE: DNA
<213> ORGANISM: Primer

<400> SEQUENCE: 6
tgaggtaccg gtggtggctc cggtattgag ggtgccagat ggctatggag cgg          53

<210> SEQ ID NO 7
<211> LENGTH: 29
<212> TYPE: DNA
<213> ORGANISM: Primer

<400> SEQUENCE: 7
tcagaatttt aatacccgtg gatttgtag                                     29

<210> SEQ ID NO 8
<211> LENGTH: 4
<212> TYPE: PRT
<213> ORGANISM: Lucilia sericata

<400> SEQUENCE: 8

Ser His Gly Tyr
1
```

POLYPEPTIDES AGAINST PLANT PATHOGENIC FUNGI

The present invention relates to polypeptides that are effective against fungi, especially against fungi causing plant diseases, and against fungi colonizing agricultural products. The invention further relates to processes for preparing such polypeptides, and to nucleic acids coding for such polypeptides. In addition, the invention relates to processes and preparations for treating plants using the polypeptides according to the invention, and to the use of the nucleic acids according to the invention for producing crops that are protected against damage from fungi.

Infections of humans by fungi present significant problems, above all for immunodeficient patients, because only a few reliable antimycotically active drugs have been known to date. Those employed most frequently include azole derivatives, such as clotrimazole or ketoconazole, which are less toxic as compared to other compounds (e.g., amphotericine B), and therefore often represent the only possibility for the therapy of fungal infections.

In addition to infections in humans and animals, fungi may also cause significant damage to plants. Yield losses because of infections of crops by fungi are among the greatest problems of modern agriculture. More than 8000 fungal species that may cause a plant disease are known. For example, *Phytophthora* species cause the rotting of potato plants, so that 20% of the potato harvest are lost per year worldwide. Of particular importance are *Fusarium* species, which infest cereal plants, such as wheat, corn and barley. For example, *Fusarium graminearum* causes diseases in these plants that are manifested as eye spots on the stalks, leaf necrosis or damaged roots, as well as cob rot in corn. The damage caused by *Fusarium graminearum* in wheat cultivation in the U.S.A. in the period from 1992 to 2001 amounted to more than 2.6 billion U.S. dollars (Schisler et al. Biological control of *Fusarium* head blight of wheat and deoxynivalenol levels in grain via use of microbial antagonists; Adv Exp Med Biol. 2002; 504: 53-69). In addition to the high yield and quality losses in infested cereals, the fungus also causes a significant contamination of the cereal with toxic metabolites (mycotoxins), which when ingested cause severe poisoning (toxicoses) with significant health problems. This in turn results in massive economical damage in the field of animal production. To date, about 100 toxins produced by *Fusarium* spp. have been identified, of which deoxynivalenol and nivalenol from the group of Trichothecenes are the most important mycotoxins in cereal cultivation. The effect of these potent inhibitors of protein synthesis includes skin toxicity and adverse affection of the nervous and digestive systems of higher animals. These substances are thus an important danger for both humans and farm animals.

Based on the quantitative proportion, dithiocarbamates and thiuram disulfides are the most important fungicides employed in agriculture, followed by azoles. The application of dithiocarbamates and thiuram disulfides is regarded with skepticism, in particular because of their water-polluting potential and their little specific mechanisms of action (Bayerisches Landesamt für Wasserwirtschaft, Leaflet No. 4.5/14, as of Jul. 25, 2005). The problems in the use of azoles, such as propiconazole or triticonazole, in plant protection mainly reside in the fact that chemically related substances with the same mechanism of action (inhibition of fungal-specific lanosterol-14α-demethylase) are also employed in medicine. Thus, there is a danger that the effectiveness of the medically employed azole antimycotics is reduced through selection for resistance in potentially human-pathogenic fungi in the environment (Report of the German Federal Institute for Health-Related Consumer Protection and Veterinary Medicine of Jun. 7, 2001). Although the formation of resistance against azoles proceeds relatively slowly and is therefore considered a moderate risk from the point of view of plant protection, it is considered that a resistance-free situation cannot be restored even today. Nevertheless, azoles are considered an indispensable element of integrated plant cultivation today.

In addition to the infestation of growing cultures, fungi also represent an important problem in the storage and stocking of seeds, cereals, fruits and other agricultural products. Colonization with fungi not only leads to immediate losses when products have to be discarded, but also carries the risk of severe poisoning if foods and feeds contaminated by mycotoxins are ingested. However, the use of fungicides in stock protection, which is possible in principle and desirable from an economical point of view, is highly restricted. In plant protection, usually enough time elapses between the application of pesticides and the harvest, so that the active substances can be degraded. In contrast, for stored crops, their sale or consumption is to be expected any time. Thus, many highly effective pesticides cannot be applied in stock protection for hygienic or toxicological reasons. Other preparations can be employed only in reduced concentrations, observing the allowable maximum levels. This results in a reduction of the success of control and in the necessity of repeating the measure, which calls the purpose of the treatment into question from an economical point of view. For example, currently no fungicides are approved for use in stock protection in Germany and Austria. Thus, no satisfactory solution exists for the control of mycotoxicogenic fungi in stocked products.

In order to improve the situation, mainly in the field of plant protection, various alternatives to synthetic low molecular weight fungicides are researched into and in part already employed. One possibility is the controlled inoculation of the crop cultures with non-virulent soil fungi, which compete with fungal pests, killing them or inhibiting the growth thereof by mechanisms that are in part incompletely researched. Mycoparasitism, antibiosis, release of siderophores, competition for habitat and nutrients, induction of systemic resistance mechanisms, and promotion of plant growth are discussed in this connection. To date, a good performance could be achieved mainly in the treatment of cocoa cultures to control the witches' broom disease caused by *Moniliophthora* (syn. *Crinipellis*) *perniciosa* in South America. A preparation formulated on the basis of *Trichoderma stromaticum* was approved in Brazil in February 2012. Other preparations based on symbiotic or endophytic *Trichoderma* species (*T. martiale, T. ovalisporum*) are under development for use against black rot of cocoa, which is caused by *Phytophthoras palmivora*, and against *Moniliophthora roreri*, the pathogen causing *Monilia* fruit rot of cocoa.

Another possible strategy for controlling harmful fungi, which has not yet entered the medical or agricultural practice, is the application of so-called antimicrobial peptides. These include gene-encoded oligopeptides that typically consist of 15 to 45 proteinogenic amino acids linked together in a linear chain (Zasloff, M. Antimicrobial peptides of multicellular organisms. Nature 2002, 415: 389-95; Boman, H. G. Antibacterial peptides: basic facts and emerging concepts. J Intern Med. 2003, 254: 197-215). Antimicrobial peptides have been found in the large majority of polycellular organisms, and are also an important component of the immune system in mammals including humans. Antimicrobial peptides are of utmost importance to the immune defense of organisms like insects and other arthropods, which do not have an adaptive immune system. Most of the known antimicrobial peptides have an amphipathic structure, wherein the hydrophilic moiety bears a positive charge. This enables peptides to interact with the typically negatively charged membrane of bacteria, and to form pore-like structures after embedding into the membrane. Since the membranes of eukaryotes usually bear no or only a weak negative charge, the activity of most antimicrobial peptides is primarily antibacterial, the effectiveness often being more pronounced against either Gram-positive or Gram-negative bacteria. A few antimicrobial peptides, such as the peptides cecropin, sarcotoxin and stomoxyn, which are characterized by an alpha-helical structure, show a broad range of activities and are also active, to various extents, against fungi, protozoans and tumor cells. However, a tendency to non-specific interactions of such antimicrobial peptides with biological membranes often also results in a hemolytic activity and thus toxicity for mammals. Further limitations to the practical application of many antimicrobial peptides are due to the reduction of the activity thereof by higher salt concentrations, often even by the physiological NaCl concentration of 150 mM (Marr et al. Antibacterial peptides for therapeutic use: obstacles and realistic outlook. Curr Opin Pharmacol. 2006, 6: 468-72). This is accounted for by the neutralization of the electrostatic interaction with the target membrane. For some antimicrobial peptides, a predominantly or exclusively fungicidal activity has been described. These antimicrobial peptides include gallerimycin, heliomicin, termicin, Alo3, drosomycin, PsD1 and NaD1 (Lobo et al. Antifungal *Pisum sativum* defensin 1 interacts with *Neurospora crassa* cyclin F related to the cell cycle. Biochemistry. 2007, 46: 987-96; van der Weerden et al. The plant defensin, NaD1, enters the cytoplasm of *Fusarium oxysporum* hyphae. J Biol Chem. 2008, 283: 14445-52). A compact three-dimensional structure stabilized by three or four disulfide bridges is characteristic of such antimicrobial peptides. Antimicrobial peptides having such structural features are referred to as defensins independently of their range of activities and of the organisms by which they are produced. Alo3 is a special case because it is the only known defensin that exclusively consists of three beta strands without the alpha-helical portions found in other defensins. The recognition of fungal membranes takes place independently of charges, at least in some cases by specific binding to neutral glucosylceramides (Aerts et al. The mode of antifungal action of plant, insect and human defensins. Cell Mol Life Sci. 2008, 65: 2069-79). Activity against both fungi and, above all, Gram-positive bacteria has further been described for metchnikowin (Levashina et al. Metchnikowin, a novel immune-inducible proline-rich peptide from *Drosophila* with antibacterial and antifungal properties. Eur J Biochem. 1995, 233: 694-700). This proline-rich peptide, which consists of 26 amino acid residues, differs from typical antimicrobial peptides by lacking a membrane-lysing activity. Shorter proline-rich antimicrobial peptides with activity predominantly against Gram-negative bacteria penetrate biological membranes without disrupting them and inhibit the chaperone protein DnaK in the interior of the cell (Kragol et al. The antibacterial peptide pyrrhocoricin inhibits the ATPase actions of DnaK and prevents chaperone-assisted protein folding. Biochemistry. 2001, 40: 3016-26). Whether this mechanism of action also holds for metchnikowin is unclear.

The application of fungicidally active peptides in medicine and cosmetics appears to be reasonable, above all, by application to the skin or mucosae, for example, in the form of powders, creams, gels, lotions, shampoos, sprays, mouth washes or toothpastes. In addition, there is a possibility of oral application or injection, for example, in the case of a life-threatening acute infection. External application is also possible in the field of plant protection and stock protection, for example, by spraying or applying powdery formulations. The preparation of active peptides can be effected synthetically, primarily by solid-phase synthesis, or by the heterological expression of corresponding nucleic acids in different host organisms. Since the preparation of oligo- and polypeptides in a pure form is complicated, alternative application forms are sought, mainly for application in plant protection. One method that is well established at least in the field of research consists in the production of genetically engineered plants into which nucleic acids coding for the active peptides to be produced were introduced. Because the constant production of such active substances by the plant is undesirable in some cases, it may be advantageous to introduce the nucleic acids in such a way that the expression thereof is under the control of promoters that are activated directly by the fungal infestation, or by the stress reactions by the plant associated therewith.

Nucleic acids coding for the defensins heliomicin and drosomycin were introduced into tobacco plants and could mediate a small, but statistically significant resistance against *Cercospora nicotianae* (Banzet et al. Expression of insect cysteine-rich antifungal peptides in transgenic tobacco enhances resistance to a fungal disease. Plant Sci. 2002, 162: 995-1006). Similarly, resistance against powdery mildew *Erysiphe cichoracearum* and *Sclerotinia minor* could be achieved by introducing nucleic acids coding for gallerimycin into tobacco plants (Langen et al. Transgenic expression of gallerimycin, a novel antifungal insect defensin from the greater wax moth *Galleria mellonella*, confers resistance to pathogenic fungi in tobacco. Biol Chem. 2006, 387: 549-57). In addition to these defensins that are specifically active against fungi, genetically engineered plants producing antimicrobial peptides with a broader range of activities were also prepared. For example, the expression in rice of a foreign gene coding for cecropin A resulted in increased resistance against the rice blast pathogen *Magnaporthe grisea* (Coca et al. Enhanced resistance to the rice blast fungus *Magnaporthe grisea* conferred by expression of a cecropin A gene in transgenic rice. Planta 2006, 223: 392-406). Increased resistance against *Fusarium solani* was achieved by the heterologous expression in potato and tobacco plants of a gene coding for an artificial hybrid peptide consisting of sequence elements of cecropin and of melittin, which occurs in bee venom (Osusky et al. Transgenic plants expressing cationic peptide chimeras exhibit broad-spectrum resistance to phytopathogens. Nat Biotechnol. 2000, 18: 1162-6; Yevtushenko et al. Pathogen-induced expression of a cecropin A-melittin antimicrobial peptide gene confers antifungal resistance in transgenic tobacco. J Exp Bot. 2005, 56: 1685-95). In barley, increased resistance against *Fusarium graminearum* and *Blumeria graminis* was observed upon introduction of a foreign gene for metchnikowin (Rahnamaeian et al. Insect peptide metchnikowin confers on barley a selective capacity for resistance to fungal ascomycetes pathogens. J Exp Bot. 2009, 60: 4105-14).

Because of these data, it is to be considered as an established fact that antimicrobial fungi are suitable in principle for controlling fungal infections in plants and in stock protection. However, only a few of these peptides having a specific activity against fungi in general and, in particular, against plant-pathogenic fungi are currently known. The use of peptides having a broad range of activities bears the risk that the growth of useful bacteria, for example, those associated with the plants as symbionts, is impeded. In addition, the presence of such peptides in products intended for human or animal ingestion may lead to interference with the natural intestinal flora and thus adversely affect health. Further problems arise from the fact that most of the known antimicrobial peptides bear a positive net charge at physiological pH values. The resulting non-specific interactions with different negatively charged biological polymers may lead to toxic effects that are difficult to predict. Thus, there is a risk of histamine release by mast cells upon contact with strongly cationic substances (Vaara, M. New approaches in peptide antibiotics. Curr Opin Pharmacol. 2009, 9: 571-6). In addition, many of the known antimicrobial peptides have an amphipathic structure, which involves a tendency to embedding in biological membranes of mammal cells, which is measurable as a hemolytic activity, so that there is further toxic potential.

EP 0 798 381 A2 discloses a polypeptide from flies of the order Diptera and the use thereof for preparing transgenic plants having an increased resistance against *Fusarium*. The entry in Database EMBL (online) of Mar. 1, 2011, EBI Accession No. JG 407441 discloses a polynucleotide from *Lucilia cuprina*. No functions associated with this polynucleotide are disclosed.

Surprisingly, it has been found that a group of polypeptides have fungicidal activity. The polypeptides according to the invention are characterized by being identical with at least 12 contiguous amino acid residues of SEQ ID No. 2, especially having at least 65% sequence homology with amino acid sequence SEQ ID No. 2.

Typically, exposure to the polypeptides according to the invention at a concentration of 1 to 1000 µM, especially 2 µM, leads to a half-maximum inhibition of the spore germination of *Fusarium graminearum*.

In one embodiment, the polypeptide according to the invention is identical with SEQ ID No. 1 or SEQ ID No. 2.

In another embodiment of the invention, the polypeptide according to the invention is effective against the growth of organisms of the genera *Fusarium* and/or *Phytophthora*.

The polypeptide according to the invention may be derivatized, especially at the N terminal, C terminal and/or in the peptide chain. The derivatization of the N terminal may include partial or complete alkylation, acylation or another N modification. The derivatization of the C terminal may include amidation, esterification or another modification of the terminal carboxy group. The derivatization of the polypeptide chain may include, in particular, a modification to improve the properties of the polypeptide according to the invention, for example, PEGylation, HESylation or the like. If desired, the polypeptide according to the invention may also be coupled to structural units having binding affinity for cellular structures of the organism against which the polypeptide according to the invention is to be employed. Suitable derivatizations for achieving modified properties of polypeptides are known to the skilled person. Derivatives of the polypeptide according to the invention having the mentioned activities are also claimed according to the invention.

In particular, the present invention relates to a polypeptide with the following sequence:

(SEQ ID NO: 2)
$Z_1$-QHGYGAGGHGQQGYGSQHSSHAPQGGHVVREQGFSGHVHEQQAGHH HEAGHHEQAGHHEQSGQQVHGQGHGYK-$Z_2$, where
$Z_1$ is the N-terminal end of the polypeptide, or a derivative of the terminal amino group of the polypeptide, or a chain of up to ten arbitrary amino acids;
$Z_2$ is the C-terminal end of the polypeptide, or a derivative of the terminal carboxy group of the polypeptide, or a chain of up to ten arbitrary amino acids.

In particular, $Z_2$ may have an amino acid sequence of SHGY-$Z_3$, wherein $Z_3$ is the C-terminal end of the polypeptide, or a derivative of the terminal carboxy group of the polypeptide, or a chain of up to six arbitrary amino acids.

In another embodiment of the invention, the polypeptide according to the invention may have D-amino acids or a D-retro-inverso peptide structure in part or completely in the peptide chain.

The invention also relates to the use of a polynucleotide coding for the polypeptide according to the invention for producing the polypeptide according to the invention, or for controlling fungi, wherein said polynucleotide has a sequence that hybridizes under conditions of stringency using 0.2×SSC at 42° C. for washing with an oligo- or polynucleotide probe selected from the group:

the complementary strand to nucleotide residues 1 to 231 from SEQ ID No. 3;
the complementary strand to nucleotide residues 1 to 102 from SEQ ID No. 3;
the complementary strand to nucleotide residues 103 to 331 from SEQ ID No. 3;
the complementary strand to nucleotide residues 18 to 251 from SEQ ID No. 4;
the complementary strand to nucleotide residues 18 to 119 from SEQ ID No. 4;
the complementary strand to nucleotide residues 120 to 251 from SEQ ID No. 4.

The present invention also relates to the use of the polypeptide according to the invention or of a nucleic acid according to the invention coding for such a polypeptide for controlling fungi, especially fungi causing plant diseases; organisms of the genera *Fusarium* and/or *Phytophthora*; organisms of the class Peronosporomycetes.

Further, the present invention relates to a process for producing the polypeptide according to the invention.

The present invention also relates to a cell, except for wild type cells of *Lucilia sericata*, containing a nucleic acid for the expression of a polypeptide according to the invention, especially a polypeptide of SEQ ID Nos. 1 or 2.

The invention also relates to a transgenic crop containing a cell according to the invention.

Figure 1:
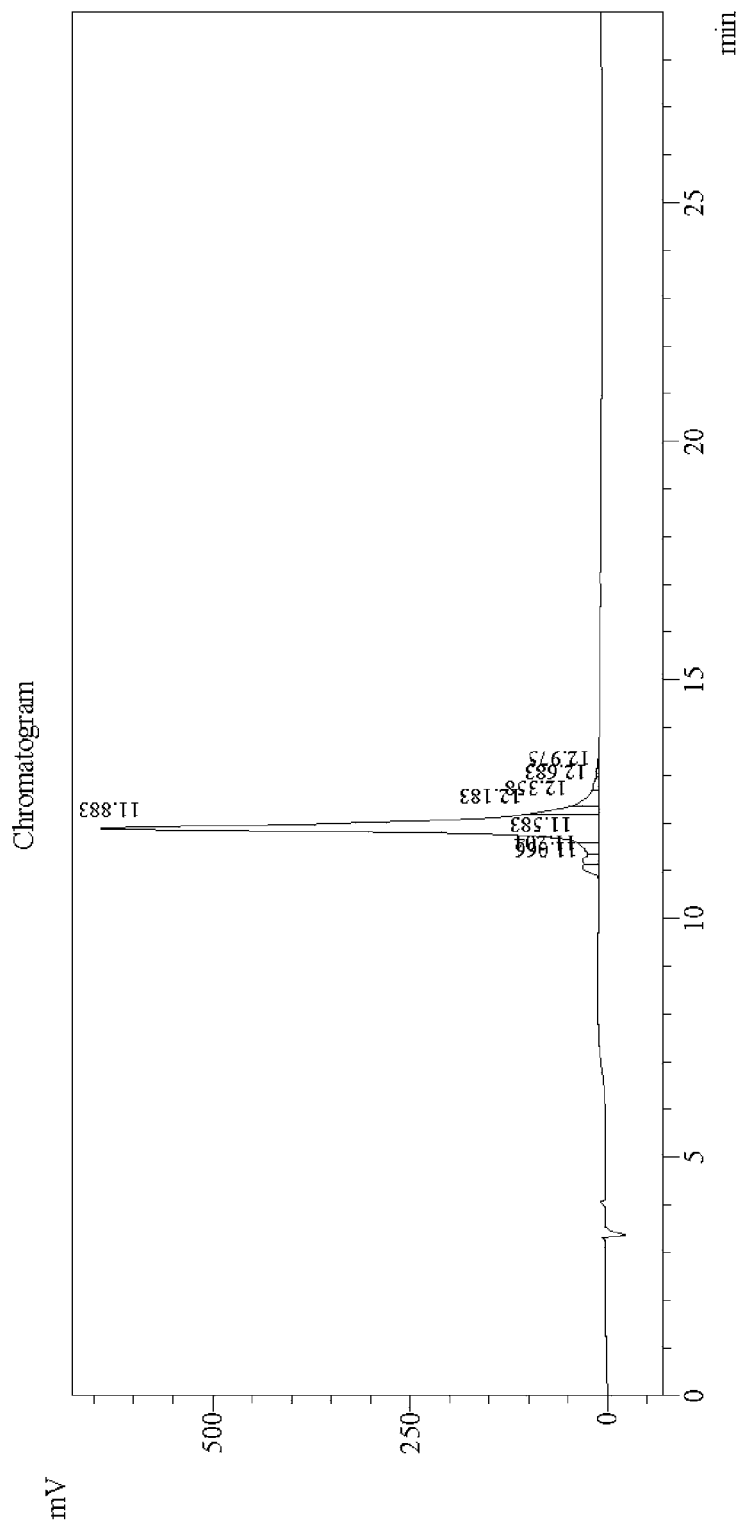
FIG. 1 shows the result of the analysis of the protein LserFCP1-77, which was prepared in a completely synthetic way, by reverse-phase chromatography and mass spectrometry.
Figure 1:
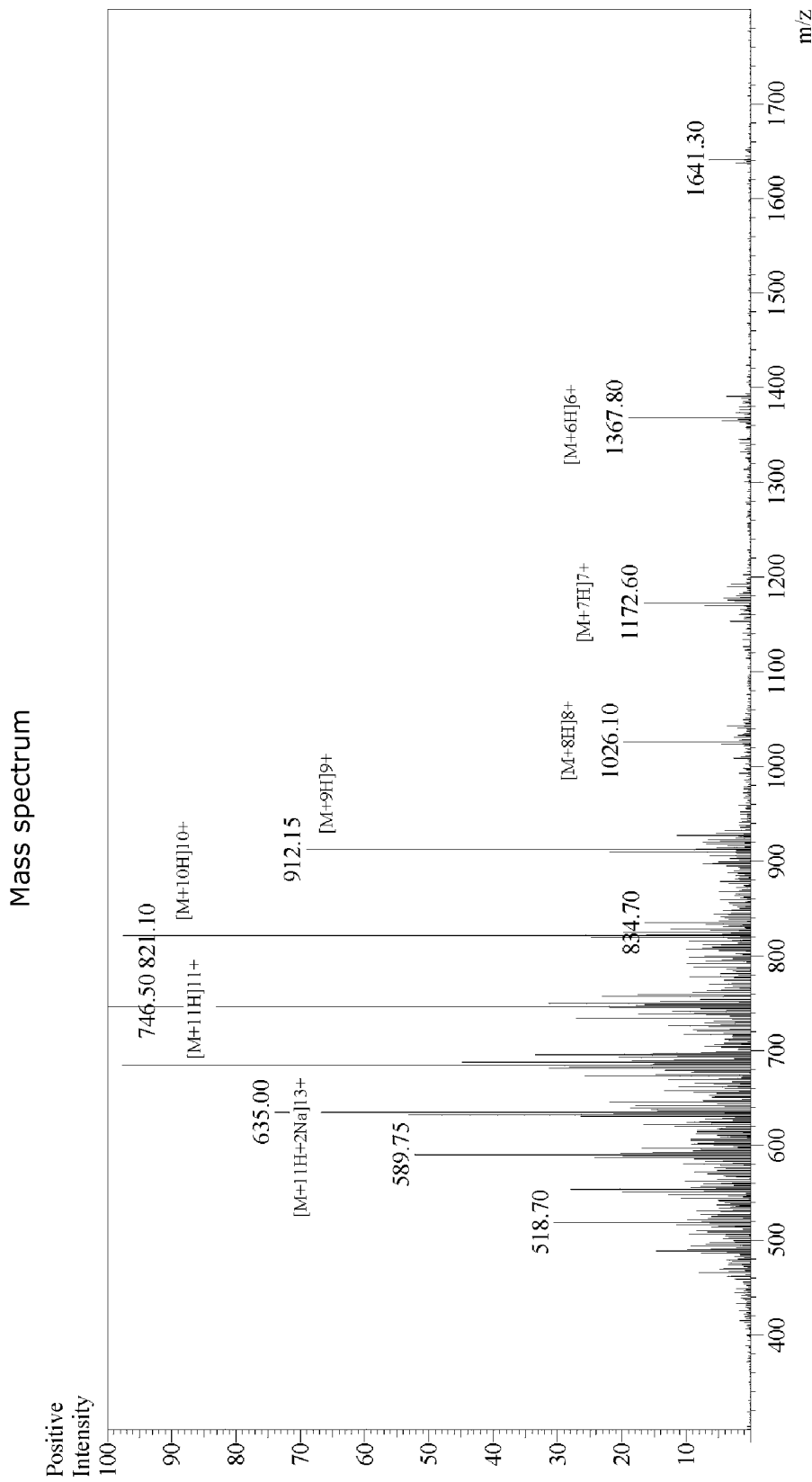

According to the invention, the term "fungicidal activity" is understood to mean the killing of fungi, the inhibition of fungal growth, and the prevention of the germination of fungal spores. These effects can be completely or partially pronounced.

According to the invention, the term "control of fungi" is understood to mean the killing of fungi, or the inhibition of the growth of existing fungi as well as the prevention of fungal colonization, and the prevention of the germination of fungal spores.

According to the invention, "fungi" is also understood to mean those organisms that are colloquially referred to as fungi (or molds), even though this does not correctly reflect the scientific evidence relating to phylogenesis. In particular, "fungi" according to the invention is intended to include representatives of the class Peronosporomycetes (former designations Oomycota or Oomycetes), including the genus *Phytophthora*.

The polypeptides according to the invention are suitable for controlling fungi that cause health-related or economical damage.

In a preferred embodiment of the invention, the polypeptides according to the invention are employed for controlling fungi that cause plant diseases or damage in the storage of agricultural products.

In another preferred embodiment of the invention, the polypeptides according to the invention are employed for controlling fungi of the genera *Phytophthora* and *Fusarium*.

The polypeptides according to the invention can be used in a pure form or in the form of different formulations for controlling fungi. For external application, the polypeptides can be diluted to form a liquid solution or suspension containing from 0.01 to 30 mg/ml of the respective polypeptide, or mixed with an extender solid for application as a dust or powder. Methods for adapting common methods for application to particular crops and pathogens are known in the literature (Methods for Evaluating Pesticides for Control of Plant Pathogens, K. D. Hickey, Ed., The American Phytopathological Society, 1986). Methods for application include the singular or periodically performed aqueous and non-aqueous spraying of plants or plant parts, seed coating, and the incorporation in spraying systems. Auxiliary additives that may be added to the formulation include stabilizers, agents for improving the dissolving performance, and wetting agents, and also agents that allow microencapsulation.

For a particularly effective control of fungi, the polypeptides according to the invention can be employed in combination with other fungicidally active substances. Also, combination with bactericidal, antiviral, nematocidal, insecticidal and other active substances common in plant protection is possible. Combination with fertilizers, plant hormones and growth regulators is also possible. One possibility of controlling fungi by means of the polypeptides according to the invention is to genetically engineer plants by introducing polynucleotide sequences coding for such polypeptides into their genetic material by a process known as transformation. Methods for preparing such genetically engineered plants according to the invention are known to the skilled person (Methods for Plant Molecular Biology, A. Weissbach, H. Weissbach, Eds., Saunders College Publishing/Harcourt Brace, June 1988; Methods in plant molecular biology and biotechnology, B. R. Glick, J. E. Thompson, CRC Press, Boca Raton, Fla., 1993). In an advantageous variant of the invention, artificial gene constructs of suitably modified vectors are incorporated into plants, plant parts or plant cells by bombardment with DNA-coated microparticles, by the so-called floral dip method, or by *Agrobacterium*-mediated transformation. Other possible methods include, for example, microinjection, chemical permeabilization, electroporation, and protoplast fusion with DNA-containing units, such as cells, minicells, protoplasts, or liposomes. In another advantageous variant of the invention, a gene coding for a polypeptide according to the invention is prepared synthetically, in which the nucleotide triplets, which code for one amino acid each, are adapted to the preferred codon usage of the genetically engineered plant. Further, it is possible to place the foreign gene to be transferred under the control of a promoter that is activatable by injury and auxine activity according to a known method, whereby an enhanced expression after fungal colonization is achieved (Rahnamaeian. Insect peptide metchnikowin confers on barley a selective capacity for resistance to fungal ascomycetes pathogens. J Exp Bot. 2009, 60: 4105-14). In an advantageous embodiment of the invention, corn and/or potato plants are genetically engineered to be able to produce the polypeptides according to the invention.

A polypeptide corresponding to SEQ ID No. 1 or No. 2 can be used for controlling fungi. In addition, it is also possible to employ polypeptides or oligopeptides resulting from truncation of the sequence or the addition of further amino acid residues.

Further, it is possible to employ variants of the polypeptide that have additional sequence elements having been added, for example, in order to achieve a higher yield in the preparation in a recombinant form, or a facilitated purification.

In some cases, it may be advantageous to employ oligopeptides consisting of at least twelve contiguous amino acid residues of SEQ ID No. 1. In addition, it may be advantageous to remove individual amino acid residues, or replace them by the residues of different amino acids. The insertion of additional amino acid residues is also possible. Such changes are also possible when proceeding from truncated or extended variants of the polypeptide. In particular, it may be advantageous to replace individual amino acid residues by those having similar physico-chemical properties. Thus, mainly residues of the amino acids are mutually interchangeable within the following groups:
Arginine and lysine;
glutamic acid and aspartic acid;
glutamine, asparagine and threonine;
glycine, alanine and proline;
leucine, isoleucine and valine;
tyrosine, phenylalanine and tryptophan;
serine and threonine.

The identification of polypeptides that are derived from SEQ ID No. 1 can be effected, for example, by the screening of genomic and/or cDNA gene libraries using known methods, which are described, for example, in Sambrook and Russell 2001 Molecular Cloning: A Laboratory Manual, Cold Spring Harbor Laboratory Press, NJ. The gene libraries can be prepared, for example, using bacteria or bacteriophages as receptor organisms. Also, the gene libraries could be in the form of sequence data electronically stored on suitable media, especially if such data were produced by means of the techniques known as Next Generation Sequencing without molecular cloning of nucleic acid molecules. As probes for the screening, there can be employed, in particular, nucleotide sequences corresponding to the complementary strand of SEQ ID No. 3 or SEQ ID No. 4, or of fragments of these sequences. The sequences of these probes may vary within the scope of the degeneracy of the genetic code, and may also contain nucleosides such as inosine, which do not naturally occur in protein-encoding nucleic acids, in order to enhance the capability of hydrogen bonding.

The screening may also be effected using antibodies raised against polypeptides corresponding to SEQ ID No. 1, SEQ ID No. 2, or fragments of these sequences.

Because of their comparatively small size, the polypeptides according to the invention can be prepared by methods of chemical peptide synthesis (Example 1). This may involve the use of known solid-phase methods, for example, according to B. Merrifield. The synthesis may be effected manually or with the aid of an automated peptide synthesizer using Fmoc or Boc protective group strategy. It is possible to synthesize the polypeptides in smaller fragments, which are subsequently linked together.

The preparation of the polypeptides according to the invention may also be effected by the heterologous expression of suitable nucleic acid constructs in different receptor organisms and receptor cells. The required methods of genetic engineering are described in Sambrook and Russell 2001 Molecular Cloning: A Laboratory Manual, Cold Spring Harbor Laboratory Press, NJ. Prokaryotic systems (for example, *Escherichia coli* or *Pseudomonas fluorescens*) or eukaryotic systems (for example, insect cells, plant cells or mammal cells) may be employed.

In a preferred embodiment of the invention, the preparation is effected in *E. coli* as a fusion polypeptide with thioredoxin and a hexahistidine sequence, wherein a specific protease recognition sequence is provided for the cleavage of the polypeptide according to the invention (Examples 2, 3 and 4).

The polypeptides according to the invention obtained by heterologous expression can be purified from cell lysates or supernatants of the genetically engineered organisms or cells by a number of known methods. Particularly suitable methods include immobilized metal ion affinity chromatography, anion-exchange chromatography, and reverse-phase chromatography (Example 3).

EXAMPLE 1

Synthetic Preparation of the Polypeptide LserFCP1-77

The polypeptide having the amino acid sequence according to SEQ ID No. 1 was prepared completely by solid-phase synthesis on a polymeric support resin. An analysis of the product by reverse-phase chromatography (column: Alltech Alltima C18 4.6×250 mm, Fischer Scientific) with an ascending methanol gradient in water yielded an essentially homogeneous peak, so that a purity of at least 80% could be assumed (FIG. 1). During the further analysis by electrospray ionization mass spectrometry (ESI-MS), a dominant molecule ion was observed at m/z 746.50, which corresponds to the eleven times protonated target molecule (FIG. 1).

EXAMPLE 2

Construction of Plasmids for the Recombinant Preparation of LserFCP1-77 and LserFCP1-73 in *Escherichia coli*

For the heterologous expression in *E. coli*, a synthetic gene was prepared that codes for the sequence of the polypeptide LserFCP1-77 (SEQ ID No. 1). The codon usage was adapted to that of the receptor organism *E. coli* K12. The gene synthesis was performed by the company Eurofins MWG Operon (Anzingerstr. 7a, 85560 Ebersberg, Germany) on a contract basis. Further sequences enabling the insertion into the vector pASK-IBA33plus were added to the coding sequence at the 5' and 3' terminals. Thus, the complete synthetically prepared polynucleotide had the sequence as shown in SEQ ID No. 4. The synthetic gene was inserted into the vector pASK-IBA33plus in an oriented way by using two BsaI restriction endonuclease cleaving sites. The thus obtained construct was used for the transformation of *E. coli* cells of the strains TOP10 and BL21.

In further experiments proceeding from the construct based on pASK-IBA33plus, the synthetic gene was recloned into the vector pET-32a(+). The recloning was performed to obtain a plasmid coding for a fusion polypeptide consisting of thioredoxin, a hexahistidine sequence, a protease recognition sequence, and the polypeptide LserFCP1-77. Two variants of this plasmid were prepared; in one, the encoded recognition sequence was specific for enterokinase, and in the other, for coagulation factor Xa. Accordingly, the plasmids were designated as pET-32-FCP-EK and pET-32-FCP-Xa.

For the construction of these plasmids, the synthetic gene was amplified by PCR, wherein the additional sequences required for the insertion into the new vector were added with the primers. pET-32-FCP-EK was constructed using the forward primer 1 consisting of a KpnI restriction site, a linking sequence, a sequence coding for the enterokinase recognition sequence, and a specific sequence coding for the first amino acid residues of the polypeptide LserFCP1-77. pET-32-FCP-Xa was constructed using the forward primer 2 consisting of a KpnI restriction site, a linking sequence, a sequence coding for the factor Xa recognition sequence, and a specific sequence coding for the first amino acid residues of the polypeptide LserFCP1-77. For both constructs, the reverse primer 3 consisting of an EcoRI restriction site, a stop codon and a specific sequence coding for the last amino acid residues of the polypeptide LserFCP1-77 was used.

```
Primer 1 (forward):
                                         (SEQ ID NO: 5)
5'-tgaggtaccgacgacgacgacaagcagcatggctatggagcgg-3'

Primer 2 (forward):
                                         (SEQ ID NO: 6)
5'-tgaggtaccggtggtggctccggtattgagggtgccagatggcta tggagcgg-3'

Primer 3 (reverse):
                                         (SEQ ID NO: 7)
5'-tcagaattttaatacccgtggatttgtag-3'
```

Figure 2:
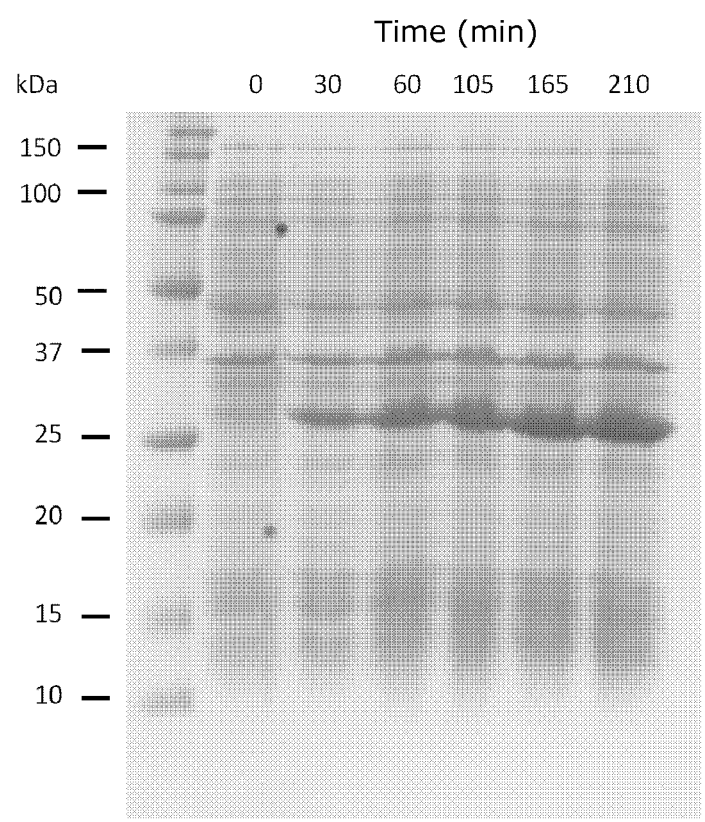
FIG. 2 shows the result of an SDS-PAGE analysis after different periods of time from the induction with IPTG of *E. coli* cells that were genetically engineered for the production of a fusion polypeptide consisting of thioredoxin, a hexahistidine sequence, a factor Xa recognition sequence, and LserFCP1-77.

The PCR products were inserted through the KpnI and EcoRI restriction sites into the vector pET-32a(+), and the constructs obtained were used for the transformation of *E. coli* cells of the strain BL21(DE3) (Novagen/Merck). The identification of transformed cells was effected by selection on ampicillin-containing nutrient medium. In its genomic DNA, the *E. coli* strain employed contains a lysogenic lambda phage on which a gene coding for T7 RNA polymerase is under the control of a lacUV5 promoter. The expression of the T7 RNA polymerase gene and thus the expression of the foreign gene being under the control of a T7 promoter on the expression plasmid is induced by adding isopropyl-beta-D-thiogalactopyranoside (IPTG). The formation of the corresponding fusion polypeptide at different times after the induction was detected by SDS PAGE followed by Coomassie blue staining (FIG. 2).

EXAMPLE 3

Production of the Recombinant Polypeptide LserFCP1-77 in *Escherichia coli*

Figure 3:
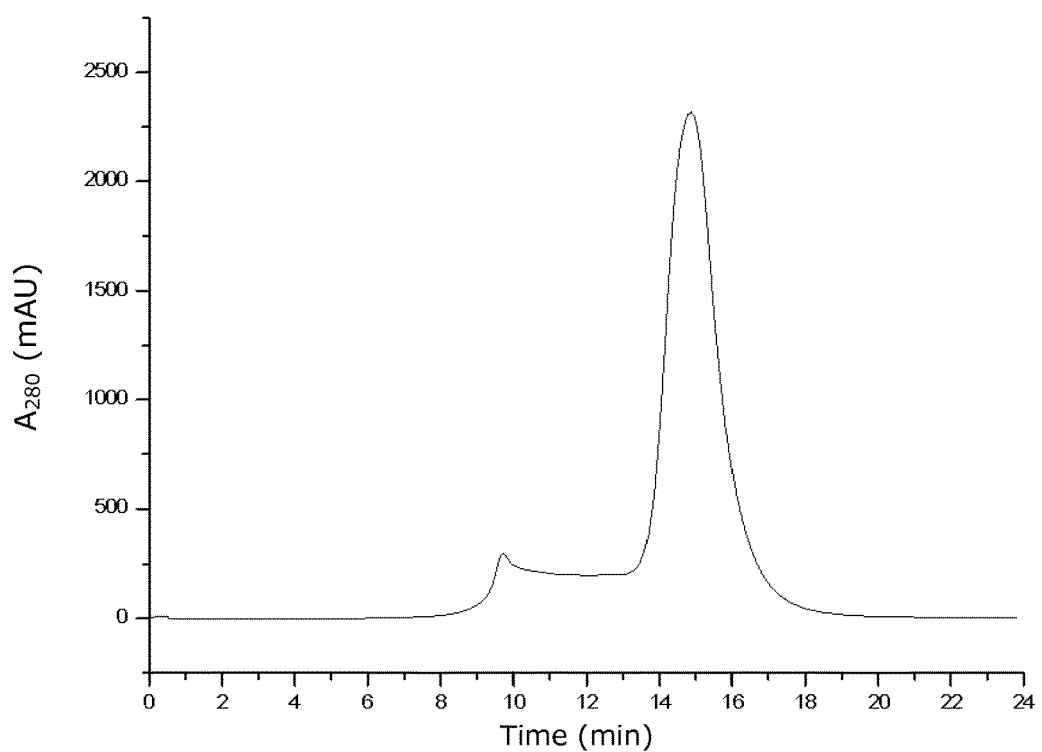
FIG. 3 shows the result of an immobilized metal ion affinity chromatography for the purification of a fusion polypeptide consisting of thioredoxin, a hexahistidine sequence, a factor Xa recognition sequence, and LserFCP1-77, and the result of the related SDS PAGE analysis.
Figure 3:
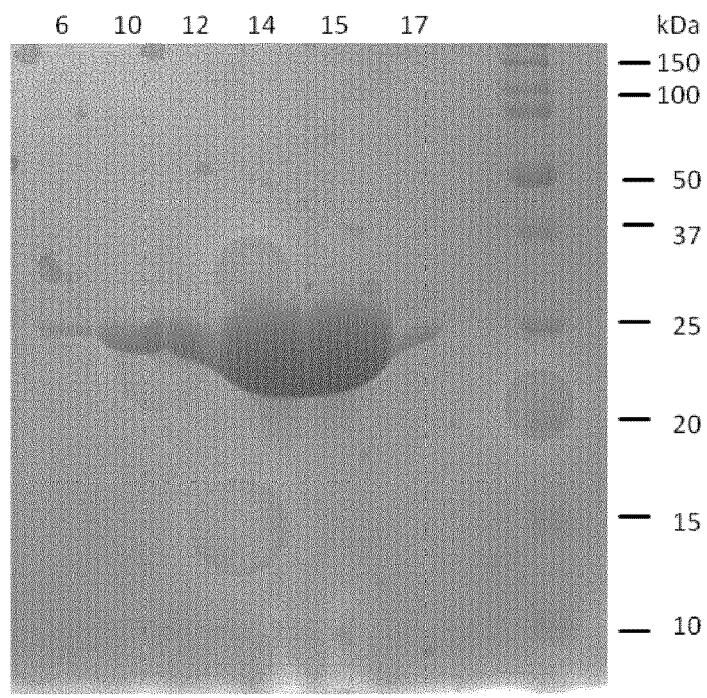

*E. coli* cells of the strain BL21(DE3) (Novagen/Merck) were transformed with the plasmid pET-32-FCP-Xa constructed as described in Example 2, and cultured in six one-liter Erlenmeyer flasks with baffles, each of which contained 400 ml of LB medium supplemented with 300 mg/l ampicillin, at 37° C. with shaking at 250 rpm. After an absorption value of 0.4 at 600 nm as observed by turbidity measurement had been achieved, the induction was effected by adding 1 mM IPTG. After the culture had been continued for 3 hours, the bacterial cells were harvested by centrifugation (10,000×g, 10 min, 4° C.). The pellet was resuspended in 200 ml of buffer A (100 mM NaCl, 30 mM Tris, pH 7.5), and the cells were lysed by shear forces in a high-pressure homogenizer (Microfluidizer M110PS, Microfluidics, 30 Ossipee Road, Newton, Mass. 02464 U.S.A.). After centrifugation (70,000×g, 30 min, 4° C.), the supernatant was filtered through a 0.22 mm membrane. The cell lysate was charged at a flow rate of 4 ml/min onto an immobilized metal ion affinity chromatographic column loaded with $Co^{2+}$ ions (16×100 mm, TALON Superflow Resin, Clontech Laboratories, 1290 Terra Bella Avenue, Mountain View, Calif. 94043, U.S.A.). The column had previously been equilibrated with buffer A. After the sample had been charged, the column was washed with buffer A until the detection at 280 nm yielded a constant value. The elution was effected with a step gradient from 30 mM to 100 mM imidazole in buffer A. The main quantity of the fusion polypeptide was eluted with the 100 mM imidazole step. An analysis by SDS PAGE followed by Coomassie blue staining yielded a purity of more than 90% (FIG. 3).

Figure 4:
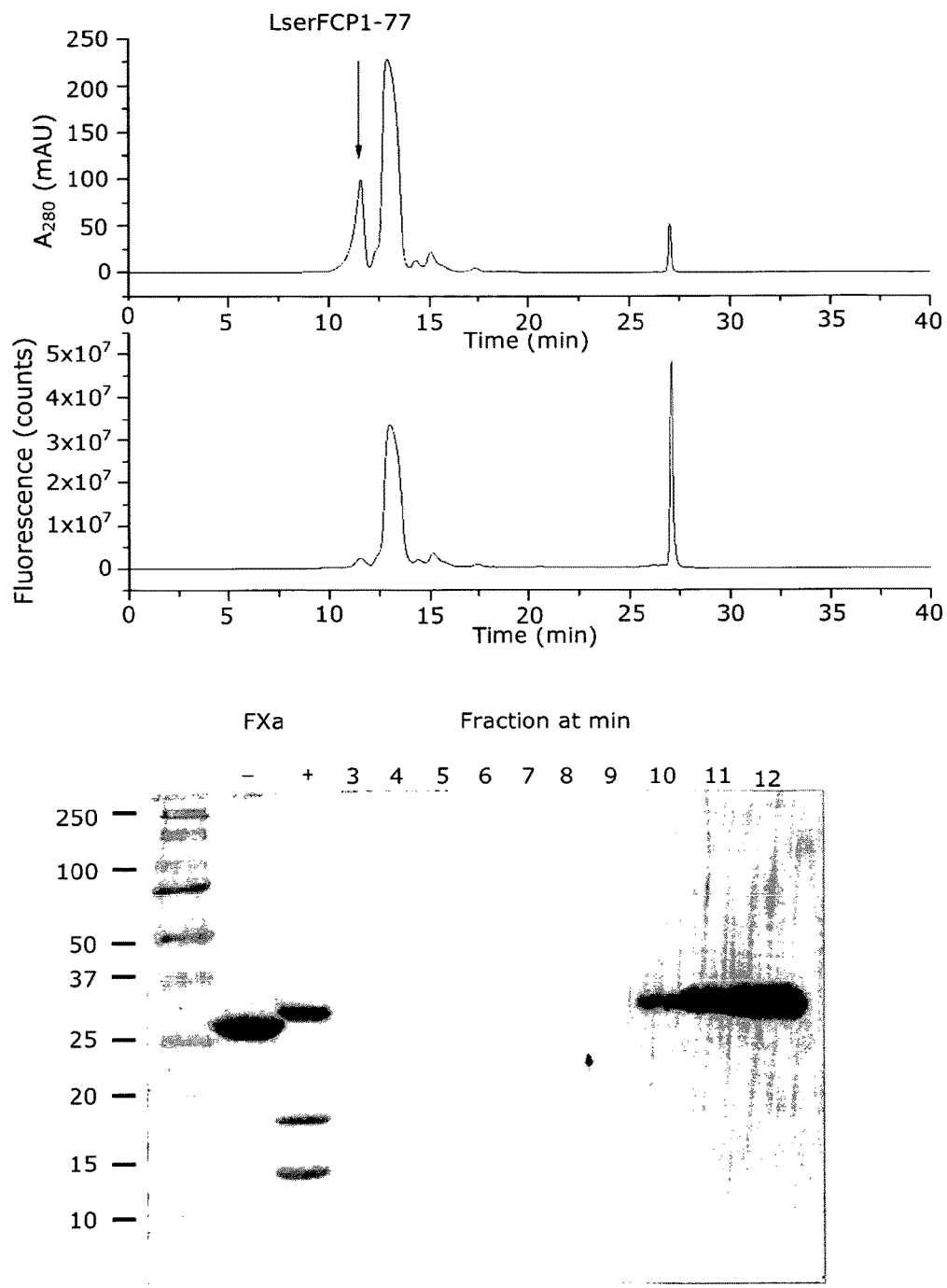
FIG. 4 shows the result of a Mono-Q chromatography for the separation of the cleavage products obtained after treatment with factor Xa of a fusion polypeptide consisting of thioredoxin, a hexahistidine sequence, a factor Xa recognition sequence, and LserFCP1-77, and the result of the related SDS PAGE analysis.
Figure 5:
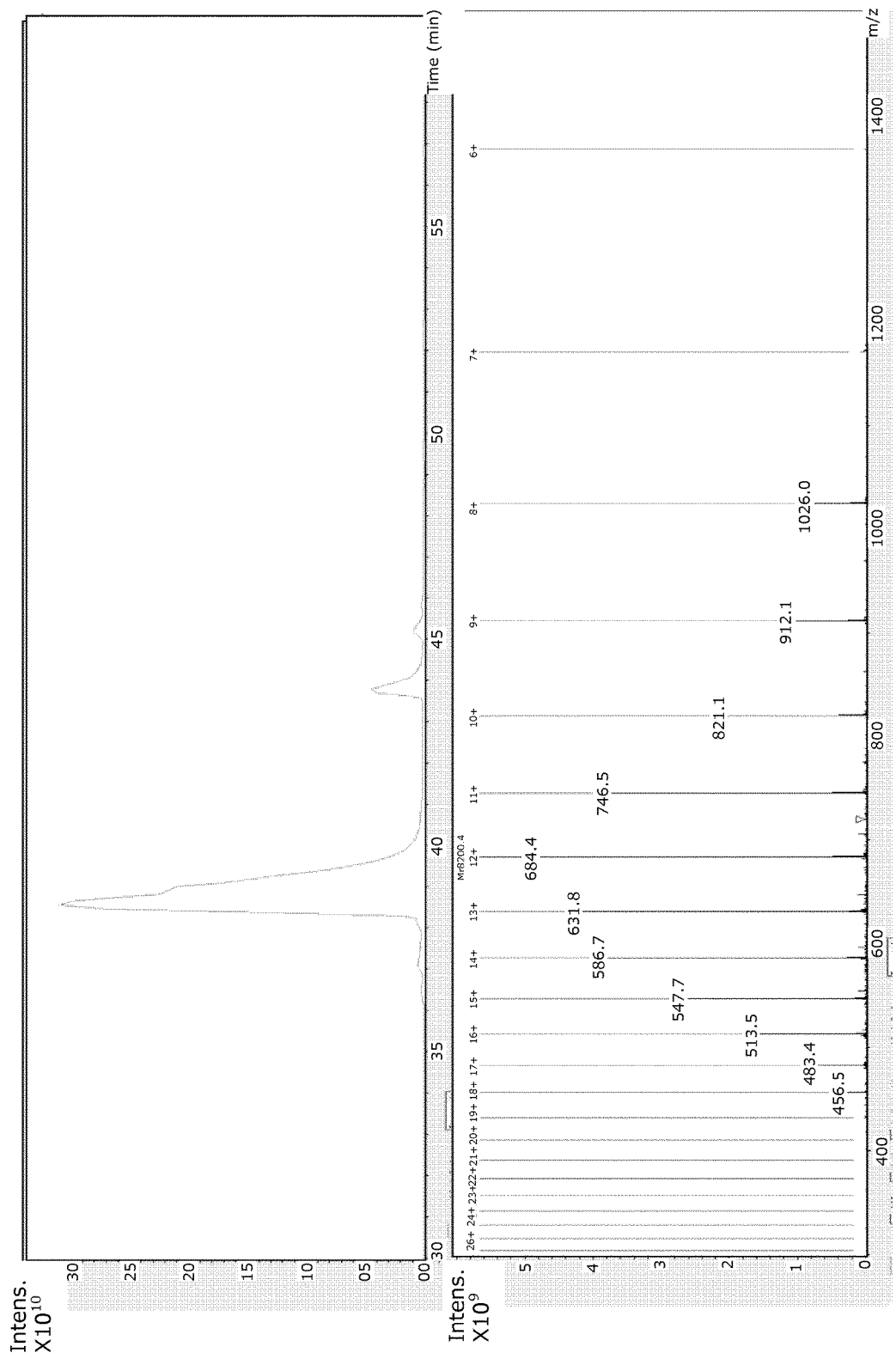
FIG. 5 shows the result of the analysis of the polypeptide LserFCP1-77, which was prepared in a recombinant form, by reverse phase chromatography and mass spectrometry.

The fusion polypeptide was rebuffered by gel permeation chromatography (HiPrep Desalting Column 26/10, GE Healthcare, Buckinghamshire, UK) in 10 mM NaCl, 10 mM Tris, pH 7.5. Ten micrograms of the fusion polypeptide was incubated with 500 units of factor Xa (Merck) in 10 ml of cleavage buffer (100 mM Tris-HCl, 20 mM NaCl, pH 7.5) for 16 h at room temperature. The reaction product was charged at a flow rate of 1 ml/min onto a strong ion-exchange column (MonoQ 5/50 GL, GE Healthcare) equilibrated with 10 mM Tris-HCl, pH 8, and the column was washed with the same buffer. The elution was effected with a gradient from 0 to 300 mM NaCl over 20 minutes. An analysis by SDS PAGE showed that the polypeptide LserFCP1-77, which was obtained as a cleaving product and eluted at 11 min, was completely separated from the remaining polypeptide components (FIG. 4). The corresponding peak in the chromatogram was visible only by detection by UV absorption, but not by fluorescence measurement. This can be explained by the absence of tryptophan residues in the amino acid sequence of the polypeptide LserFCP1-77. In an SDS PAGE analysis, LserFCP1-77 exhibited an apparent molecular mass of 30 kDa instead of the expected 8.2 kDa. This atypical electrophoretic behavior is possibly accounted for by ineffective binding of SDS molecules to the polypeptide. The identity of the polypeptide was checked by reverse-phase chromatography (column: BioBasic 8, 2×150 mm, Dionex; gradient: 10-80% acetonitrile in water with 0.1% formic acid) with direct injection into an ESI mass spectrometer (amaZon ETD, Bruker Daltonik, Fahrenheitstr. 4, D-28359 Bremen). The predominant molecular ion observed at m/z 684 corresponded to the twelve times protonated target molecule (FIG. 5).

EXAMPLE 4

Production of the Recombinant Polypeptide LserFCP1-73 in *Escherichia coli*

Figure 6:
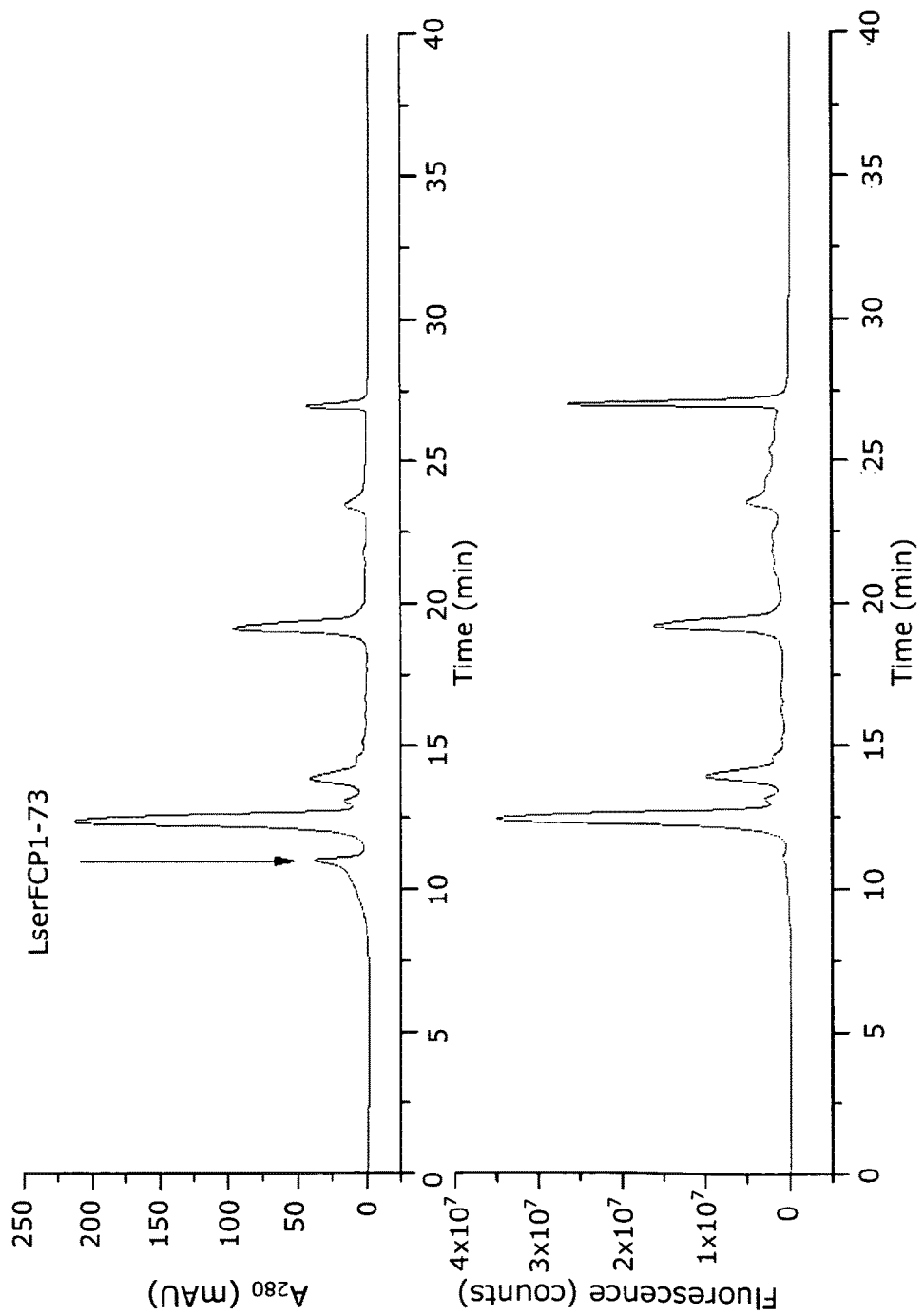
FIG. 6 shows the result of a Mono-Q chromatography for the separation of the cleavage products obtained after treatment with enterokinase of a fusion polypeptide consisting of thioredoxin, a hexahistidine sequence, an enterokinase recognition sequence, and LserFCP1-77, and the result of the mass-spectrometric analysis of the obtained polypeptide LserFCP1-73.
Figure 6:
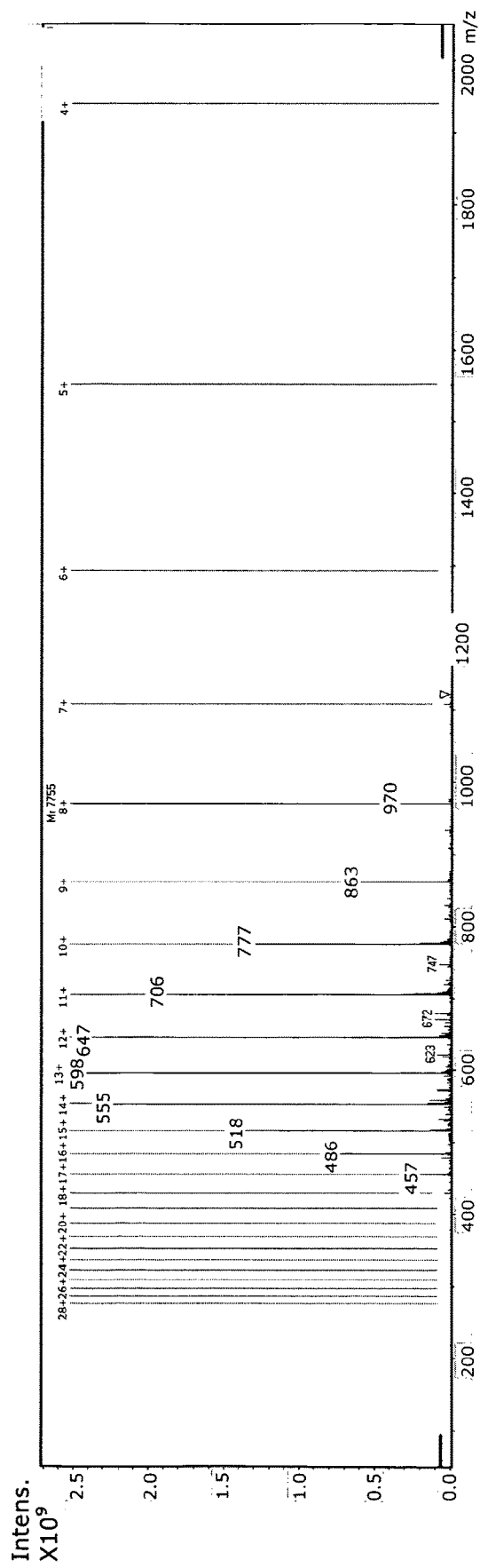

*E. coli* cells of the strain BL21(DE3) (Novagen/Merck) were transformed with the plasmid pET-32-FCP-EK constructed as described in Example 2. The culturing of the cells and the processing of the cell lysate were performed by analogy with the operations described in Example 3, except that 0.1 units of enterokinase (Novagen) were employed for cleaving the fusion polypeptide. In this case too, it was possible to separate the target molecule by anion-exchange chromatography (FIG. 6). However, the mass-spectrometric analysis (micrOTOF II, Bruker Daltonik, Fahrenheitstr. 4, D-28359 Bremen) showed that the expected polypeptide LserFCP1-77 had not been formed (FIG. 6). The data showed clearly that the polypeptide that had formed was LserFCP1-73 having a molecular mass of 7755 Da. This is to be explained by the fact that the last four amino acid residues of the LserFCP1-77 sequence had been cleaved off, apparently by a non-characteristic activity of the enterokinase.

EXAMPLE 5

Determination of the Activity of LserFCP1-77 Against *Fusarium graminearum*

*Fusarium graminearum* (Strain IFA 65)
Source of supply: Interuniversitary Department for Agricultural Biotechnology of Tulln, Austria
Reference: Steiner B, Kurz H, Lemmens M, Buerstmayr H. Differential gene expression of related wheat lines with contrasting levels of head blight resistance after *Fusarium graminearum* inoculation. Theor Appl Genet. 2009 February; 118(4): 753-64.

Figure 7:
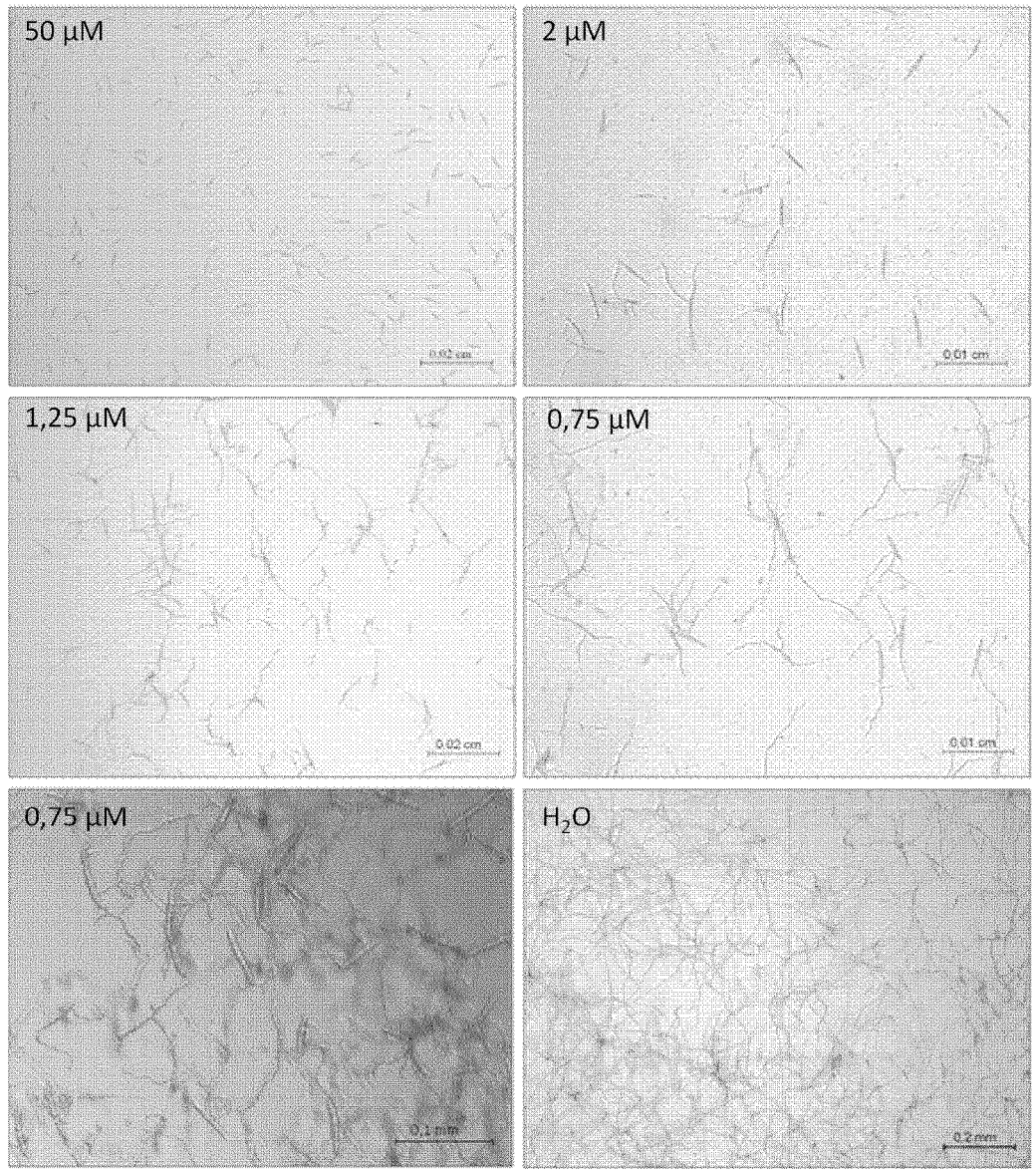
FIG. 7 shows the result of tests on the polypeptide LserFCP1-77 for inhibition of the spore germination of *Fusarium graminearum* at the stated concentrations as compared to a water control.
Figure 8:
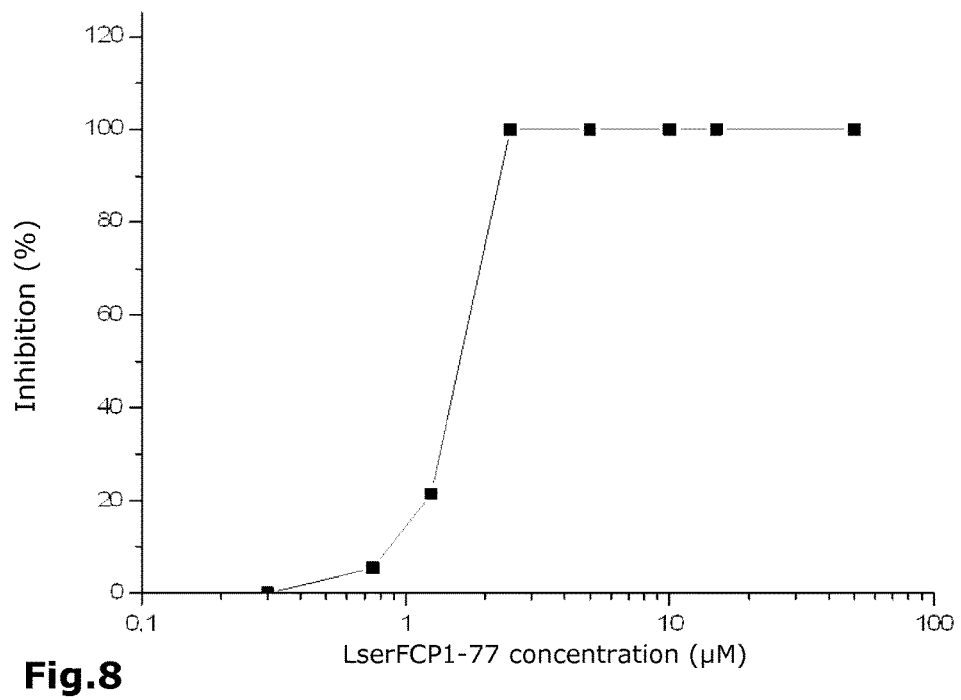
FIG. 8 shows the dose-effect relationship for the inhibition of the spore germination of *Fusarium graminearum* by LserFCP1-77.

*Fusarium graminearum* was cultured on SNA-agar plates at room temperature to sporulation. The spores were swept off the plate with water, adjusted to a density of 20,000 spores/ml, and stored at 4° C. until further use. For performing the tests, 0.05 ml each of the spore suspension was combined with 0.05 ml each of differently concentrated LserFCP1-77 solutions in the wells of a 96-well microtitration plate. After incubation for 24 h at room temperature, the spores were examined microscopically for germination using objective lenses with 4 fold and 10 fold magnifications. The result was documented photographically (FIG. 7). The proportion of germinated and non-germinated spores was counted, and the data obtained were used for the graphic representation of the dose-effect relationship (FIG. 8). The thus established concentration in which a half-maximum inhibition occurred was at 1.6 µM. In addition, the length of the hyphae formed by the germinated spores was observed as a semiquantitative measure of the inhibition (FIG. 7).

EXAMPLE 6

Determination of the Activity of LserFCP1-73 Against *Fusarium graminearum*

Figure 9:
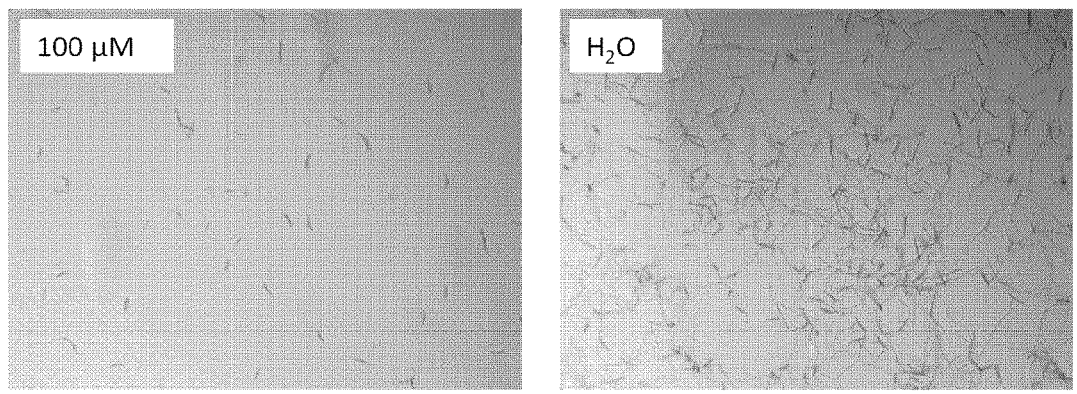
FIG. 9 shows the result of tests on the polypeptide LserFCP1-73 for inhibition of the spore germination of *Fusarium graminearum* at the stated concentrations as compared to a water control.

The effectiveness of LserFCP1-73 at a concentration of 100 µM was determined as compared to a water control by means of the test system described in Example 5. A complete inhibition of spore germination by LserFCP1-73 was observed (FIG. 9).

EXAMPLE 7

Determination of the Activity of LserFCP1-77 Against *Phytophthora parasitica*

*Phytophthora parasitica* (Isolate 329)
Source of supply: INRA (institut national de la recherche agronomique), France Reference: Keller H, Pamboukdjian N, Ponchet M, Poupet A, Delon R, Verrier J L, Roby D, Ricci P. Pathogen-induced elicitin production in transgenic tobacco generates a hypersensitive response and nonspecific disease resistance. Plant Cell. 1999 February; 11(2): 223-35.

Figure 10:
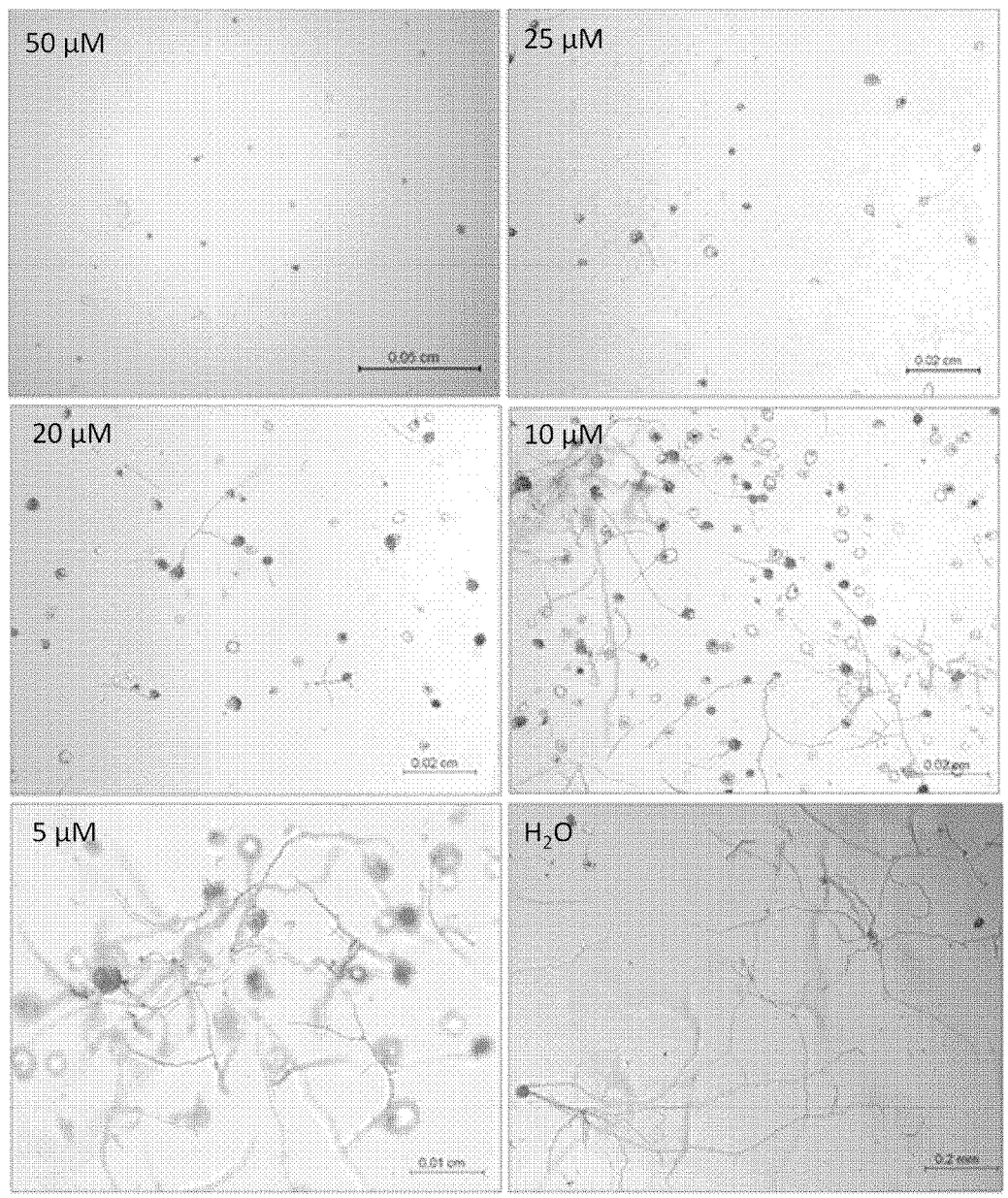
FIG. 10 shows the result of tests on the polypeptide LserFCP1-77 for inhibition of the spore germination of *Phytophthora parasitica* at the stated concentrations as compared to a water control.

*Phytophthora parasitica* was cultured on Rye B agar plates for 8 days at 25° C. The sporangia were washed off with water, and the sporangia suspension obtained was incubated for 4 h at 4° C. to induce the formation of zoospores. After 1:50 dilution in RPMI 1640 medium, the spore density was determined and adjusted to 20,000 spores/ml. The further performance of the test was effected by using the methods described in Example 5. The result was also documented photographically (FIG. 10).

SEQUENCE LISTINGS

The amino acids were abbreviated according to the IUPAC nomenclature as follows: alanine A, arginine R, asparagine N, aspartic acid E, cysteine C, glutamic acid D, glutamine Q, glycine G, histidine H, isoleucine I, leucine L, lysine K, methionine M, phenylalanine F, proline P, serine S, threonine T, tryptophan W, tyrosine Y, valine V

```
SEQ ID NO: 1-LserFCP1-77
QHGYGAGGHGQQGYGSQHSSHAPQGGHVVREQGFSGHVHEQQAGHHHEAG

HHEQAGHHEQSGQQVHGQGHGYKSHGY (SEQ ID NO: 1)

SEQ ID NO: 2-LserFCP1-73
QHGYGAGGHGQQGYGSQHSSHAPQGGHVVREQGFSGHVHEQQAGHHHEAG

HHEQAGHHEQSGQQVHGQGHGYK (SEQ ID NO: 2)

SEQ ID NO: 3-L. sericata cDNA coding for
LserFCP1-77
5'-CAACACGGCTATGGTGCCGGTGGCCATGGCCAACAAGGCTATGGTAG

CCAACATAGCAGTCATGCTCCCCAAGGTGGACATGTTGTCCGTGAACAAG

GTTTTAGTGGTCATGTTCATGAACAACAGGCTGGGCATCATCATGAAGCT

GGCCATCATGAGCAAGCTGGTCATCATGAACAATCTGGTCAACAAGTTCA

TGGTCAAGGTCATGGCTATAAAAGTCATGGTTAT-3'
(SEQ ID NO: 3)

SEQ ID NO: 4-synthetic gene with E. coli adapted
codon usage coding for LserFCP1-77
The non-coding sequence segments added for
cloning are printed in oblique characters.

5'-ATGGTAGGTCTCAAATG CAG CAT GGC TAT GGA GCG GGT

GGA CAT GGC CAG CAG GGT TAC GGC TCT CAG CAC AGC

AGT CAT GCT CCG CAA GGT GGC CAT GTC GTT CGC GAA

CAG GGC TTT TCC GGT CAC GTA CAC GAG CAG CAA GCA

GGC CAT CAC CAT GAA GCC GGC CAT CAC GAA CAA GCG

GGT CAC CAT GAG GAG TCA GGG CAG CAA GTG CAT GGG

CAA GGT CAT GGC TAC AAA TCG CAC GGG TAT

TAAAGCGCTGAGACCTACCAT-3' (SEQ ID NO: 4)
```

The invention claimed is:

1. A polypeptide comprising an amino acid sequence identical with SEQ ID NO: 1 or SEQ ID NO: 2, wherein (i) the N-terminal end is derivatized by partial alkylation, complete alkylation, or acylation, (ii) the C-terminal end is derivatized by amidation or esterification, (iii) the peptide chain is derivatized by PEGylation or HESylation, or (iv) a combination thereof.

2. The polypeptide according to claim 1, which leads to a half-maximum inhibition of the spore germination of *Fusarium graminearum* at a concentration of 1 to 1000 μM.

3. The polypeptide according to claim 1, which is effective against the growth of organisms of the genera *Fusarium* and/or *Phytophthora*.

4. The polypeptide according to claim 1, having the following sequence (SEQ ID NO: 2)
$Z_1$-QHGYGAGGHGQQGYGSQHSSHAPQGGHVVREQGFSGHVHE

QQAGHHHEAGHHEQAGHHEQSGQQVHGQGHGYK-$Z_2$, where $Z_1$ is the N-terminal end of the polypeptide, the derivatized N-terminal amino group of the polypeptide, or a chain of up to ten arbitrary amino acids; and $Z_2$ is the C-terminal end of the polypeptide, the derivatized C-terminal carboxy group of the polypeptide, or a chain of up to ten arbitrary amino acids;

wherein at least one of $Z_1$ or $Z_2$ is derivatized or a chain of up to ten arbitrary amino acids.

5. The polypeptide according to claim 4, wherein $Z_2$ has an amino acid sequence of SHGY-$Z_3$, wherein $Z_3$ the C-terminal end of the polypeptide, the derivatized C-terminal carboxy group of the polypeptide, or a chain of up to six arbitrary amino acids, and wherein $Z_1$ is derivatized or has a chain of up to ten arbitrary amino acids or $Z_3$ is derivatized or has a chain of up to six amino acids.

6. The polypeptide according to claim 1, wherein the polypeptide has D-amino acids in part, D-amino acids completely, or a D-retro-inverso peptide structure.

7. A polynucleotide coding for the polypeptide according to claim 1.

8. A method of using the polypeptide according to claim 1 the method comprising applying the polypeptide to a plant for controlling fungi or oomycetes.

9. A cell, except for wild type cells of *Lucilia sericata*, wherein said cell contains a nucleic acid for the expression of a polypeptide according to claim 1.

10. A transgenic crop containing a cell according to claim 9.

11. The polypeptide according to claim 1, which leads to a half-maximum inhibition of the spore germination of *Fusarium graminearum* at a concentration of 2 μM.

12. The method according to claim 8, wherein the fungi cause plant diseases.

13. The method according to claim 8, wherein the fungi are selected from the group consisting of the genus *Fusarium* and the genera *Phytophthora*, and the oomycetes are from the class Peronosporomycetes.

* * * * *